United States Patent [19]

Turner

[11] Patent Number: 5,516,438

[45] Date of Patent: *May 14, 1996

[54] FABRIC SOFTENING

[75] Inventor: Graham A. Turner, Merseyside, England

[73] Assignee: Lever Brothers Company, Division of Conopco, Inc., New York, N.Y.

[*] Notice: The portion of the term of this patent shall not extend beyond the expiration date of Pat. No. 5,422,021.

[21] Appl. No.: 413,575

[22] Filed: Mar. 30, 1995

Related U.S. Application Data

[63] Continuation-in-part of Ser. No. 195,594, Feb. 14, 1994, Pat. No. 5,422,021, which is a continuation of Ser. No. 890,333, May 26, 1992, abandoned, which is a continuation of Ser. No. 580,890, Sep. 11, 1990, abandoned.

[30] Foreign Application Priority Data

Sep. 19, 1989 [GB] United Kingdom ............... 8921168

[51] Int. Cl.$^6$ .................................... D06M 13/46
[52] U.S. Cl. ...................... 252/8.8; 252/8.6; 252/541; 252/544; 252/546; 554/110; 564/291; 564/296
[58] Field of Search .................... 252/8.6, 8.8, 541, 252/544, 546, 547; 554/110; 564/291, 296

[56] References Cited

U.S. PATENT DOCUMENTS

| | | | |
|---|---|---|---|
| 3,872,138 | 3/1975 | Ogata | 252/8.8 |
| 3,915,867 | 10/1975 | Kang et al. | 252/8.8 |
| 4,137,180 | 1/1979 | Naik et al. | 252/8.8 |
| 4,308,024 | 12/1981 | Wells | 8/137 |
| 4,429,859 | 2/1984 | Steiner et al. | 252/8.8 |
| 4,767,547 | 8/1988 | Straathof et al. | 252/8.8 |
| 4,830,771 | 5/1989 | Ruback et al. | 252/8.8 |
| 4,963,274 | 10/1990 | Ruback et al. | 252/8.75 |
| 4,965,100 | 10/1990 | Leigh et al. | 252/8.8 |
| 5,288,417 | 2/1994 | Bauer et al. | 252/8.8 |
| 5,422,021 | 6/1995 | Turner | 252/8.8 |

*Primary Examiner*—Anthony Green
*Attorney, Agent, or Firm*—A. Kate Huffman

[57] ABSTRACT

A method of preparing a fabric softening material which comprises a quaternary ammonium material and at least one $C_{8-28}$ alkyl or alkenyl group connected to the molecule via an ester linkage. The process comprises the step of reacting a base material with an alkyl or alkenyl group continuing material, such that at least one alkyl or alkenyl group is connected to the base material via an ester linkage. The reaction between the base material and the alkyl or alkenyl group containing material is carried out in the presence of more than 10 mole percentage excess of the alkyl or alkenyl group containing material to the base material. The excess material being effective to lower the pour point of the softener material.

6 Claims, 1 Drawing Sheet

FABRIC SOFTENING

RELATED APPLICATIONS

This application is a continuation-in-part application of U.S. Ser. No. 08/195,594, filed Feb. 14, 1994, now U.S. Pat. No. 5,422,021, which is a continuation of U.S. Ser. No. 07/890,333, filed May 26, 1992, now abandoned, which is a continuation of U.S. Ser. No. 07/580,890, filed Sep. 11, 1990, now abandoned.

BACKGROUND OF THE INVENTION

This present invention relates to a method of preparing a fabric softening material, in particular to a method of preparing a softening material comprising one or more $C_8$–$C_{28}$ alkyl or alkenyl groups which are connected to the softener molecule via an ester linkage.

It has been proposed in U.S. Pat. No. 4,767,547 corresponding to EP 239 910 (Procter & Gamble) to incorporate ester linked quaternary ammonium compounds in fabric softening compositions. U.S. Pat. No. 3,915,867 (Stepan) discloses the use of N-methyl,N,N-di(beta-$C_{14-18}$ acyloxyethyl) N-beta-hydroxy ethyl ammonium methosulphate in softening compositions. Other ester linked softener materials are described in U.S. Pat. No. 4,137,180 (Lever Brothers). Softener materials comprising ester linkages are especially preferred for use in fabric conditioning compositions for environmental reasons.

A problem with softener materials comprising ester linkages is that they tend to have a relatively high pour point. Pour point can be defined as the lowest temperature at which an active material can be observed to flow or at which temperature the active becomes mobile. (As explained in The Analysis of Fats and Oils by V. C. Mehlenbacher, The Garrard Press, Champaign, Ill. 1960). A high pour point renders the softener materials difficult to process. For example, the softener materials as described in U.S. Pat. No. 4,137,180 (Lever Brothers) have high pour points meaning that they are hardly pumpable at ambient temperature and are difficult to disperse in water.

It is an object of the present invention to solve the above mentioned problem and to provide a process for the preparation of ester linked softener materials.

In the preparation of ester linked softener materials it is known to use a base material, which is similar to the final softener molecule, excepting that it does not comprise the alkyl or alkenyl groups connected to the molecule via an ester linkage. This base material is then reacted with one or more alkyl or alkenyl group containing materials, such that one or more alkyl or alkenyl groups become attached to the base material via an ester-linkage. Finally the material may optionally be subjected to further processing steps, for example quaternization or neutralization, to form the end-product.

For example in U.S. Pat. No. 3,915,867 (Stepan) a process for the preparation of an ester-linked quaternary ammonium material is disclosed, wherein triethanolamine as the base material in the presence of a sodium methoxide solution is reacted with a fatty acid methyl ester mixture in an esterification reaction to form a molecule wherein two alkyl chains are connected to the base molecule via an ester linkage. The molar ratio of fatty acid methyl ester to triethanolamine is 2:1.

In U.S. Pat. No. 4,137,180 (Lever Brothers) a similar method of preparation is disclosed, wherein di-methyl-amino-propane 1,2-diol as the base material is reacted with tallow fatty acids in an esterification reaction to form a molecule, wherein two alkyl groups are connected to the base molecule via ester links.

The described process may use an excess of tallow fatty acids to base material, although this is not preferred. It is further stated that if the molar fatty acid to base is greater than 2:1, free fatty acid remains in the product and is neutralized by alkali at a later step to form soap, which is also not desirable.

U.S. Pat. No. 4,137,180 further requires that the ester-linked quaternary ammonium material must be purified, for example, by recrystallization to remove excess fatty acid from the final product.

An alternative method of preparation is disclosed wherein glycidyl trimethyl ammonium chloride as the base material is reacted with tallow fatty acid anhydride to form a mixture of monoester and diester quaternary ammonium salt in a weight ratio of 3:1 diester to monoester.

SUMMARY OF THE INVENTION

It has now been found, that the pour point of the obtained materials can markedly be reduced when the reaction of the base-material with the alkyl or alkenyl containing material is carried out in the presence of a 10% mole excess of alkyl or alkenyl group containing material.

DETAILED DESCRIPTION OF PREFERRED EMBODIMENTS

Figure 1:
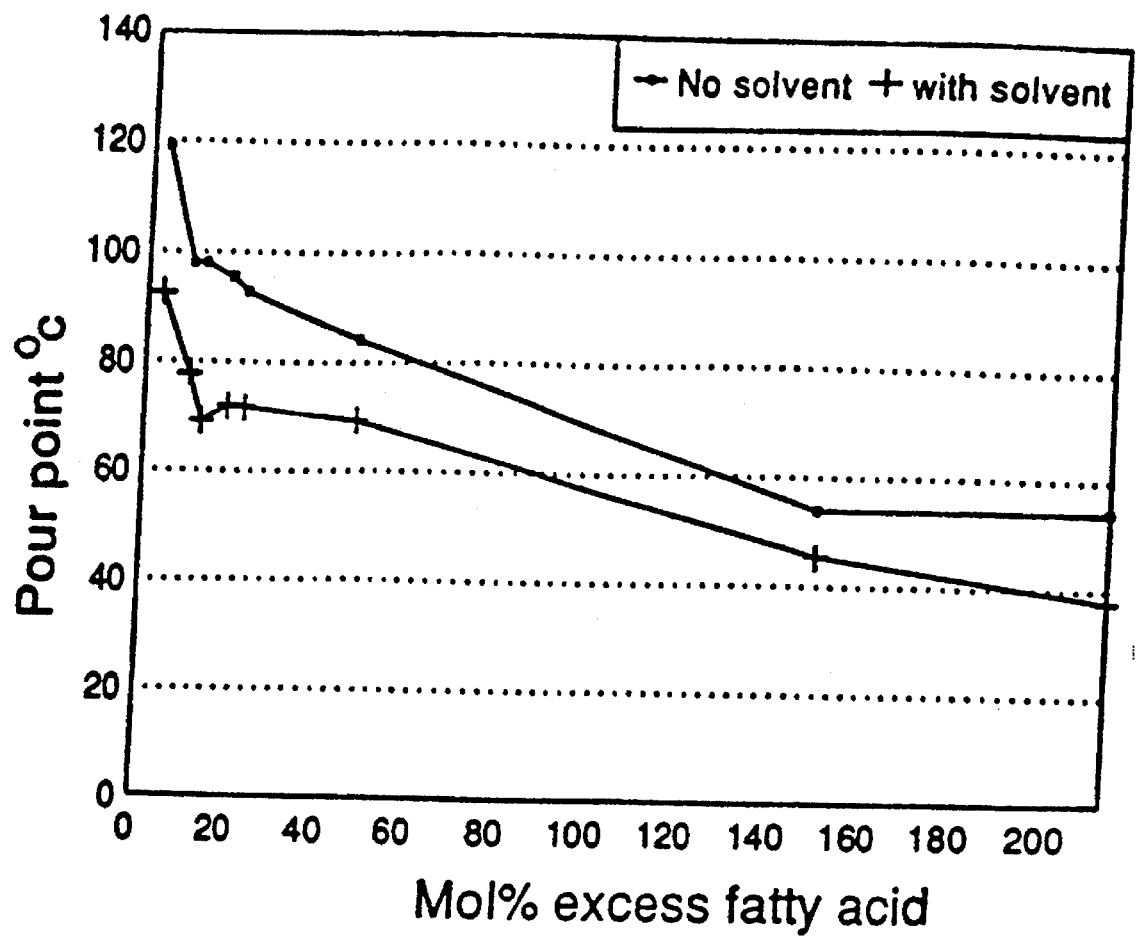
FIG. 1 is a graph of the pour point values of a softening composition containing amounts of excess fatty acid according to the invention.

The alkyl or alkenyl group containing material is in excess when the number of moles of alkyl or alkenyl group containing material is greater than the number of moles of the base material multiplied by the number of sites capable of forming an ester link in the base material. For example in U.S. Pat. No. 4,137,180 a base material is di-methyl-amino-propane 1,2 diol which has two sites capable of forming an ester link. Molar ratios of alkyl or alkenyl group containing material to base material greater than 2:1 are thus in excess for this base material.

Accordingly, the present invention provides a method of preparing a softening material which comprises a quaternary ammonium group comprising the step of reacting a base material with an alkyl or alkenyl group containing material such that at least one alkyl or alkenyl group is connected to the base material via an ester linkage wherein the reaction takes place in the presence of more than a 10 mole % excess of the alkyl or alkenyl group containing material, said excess being effective to lower the pour point of the softening material, and wherein the softening material has a weight ratio of diester material to monoester material greater than 3:1.

Pour point is the lowest temperature at which the active material can be observed to become mobile or to flow. Pour point may be equated with the melting point of a solvent free active. In the presence of a solvent, the pour point could be described as a dissolution temperature rather than a melting point. Thus, to avoid any ambiguity the term pour point will be used in this description.

Preferably the reaction is carried out such that two $C_{8-28}$ alkyl or alkenyl groups are attached to the base-material via ester linkages. Most preferably the method of the invention is used to prepare softener material of the formula:

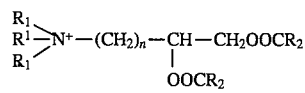

wherein each $R_1$ group is independently selected from $C_{1-4}$ alkyl, alkenyl or hydroxyalkyl groups; and each $R_2$ group is independently selected from $C_{8-28}$ alkyl or alkenyl groups; n is an integer from 0–5.

A suitable base material for preparing these materials is a tertiary amine comprising two $R_1$ groups and one 1,2 diol-group connected to the nitrogen atom via the $(CH_2)_n$ group.

The reaction between the base material and the alkyl or alkenyl group containing material will result in the formation of one or more ester linkages in the molecule.

Preferably the base-material comprises one or more hydroxy groups for reaction with the alkyl or alkenyl containing materials. The alkyl or alkenyl group containing materials, preferably are fatty acids, their soaps or their $C_{1-6}$ esters. Most preferably the base material comprises two hydroxy groups which react with two free fatty acid molecules to form two ester linkages.

According to the method of the invention the esterification reaction is carried out in the presence of a greater than 10 mole % excess of alkyl or alkenyl group based on the number of moles of alkyl or alkenyl group containing material multiplied by the number of sites capable of forming an ester link in the base material. Preferably the amount of alkyl or alkenyl group containing material in excess of the reacting alkyl or alkenyl group containing material is more than 20 mole %, more preferred the excess is more than 50 mole %, preferably between 100 and 500 mole %, most preferred between 200 and 400 mole %.

The excess of alkyl or alkenyl groups may come from any source, although the following type of alkyl or alkenyl group containing materials are preferred: $C_{8-28}$ fatty acids, alcohols, ketones, esters or mixtures thereof.

Preferably the excess of alkyl or alkenyl group containing materials is the same material as the alkyl or alkenyl material used for reacting with the base material. For example in the preparation of softener materials according to U.S. Pat. No. 4, 137,180 (Lever Brothers) the base material is reacted with a free fatty acid. For modifying this process according to the invention the reaction between the base material and the free fatty acid is carried out in the presence of an excess of materials which contain alkyl or alkenyl groups. This excess material may be selected from any alkyl or alkenyl groups containing materials such as the above mentioned $C_{8-28}$ fatty acids, alcohols, ketones, esters or mixtures thereof, preferably however the excess of alkyl or alkenyl groups comes from an excess of fatty acid materials.

Therefore a preferred method of preparing softener materials according to the invention involves the reaction of the base-material with a fatty acid, a soap thereof or a $C_{1-6}$ ester thereof, wherein a greater than 10 mole % excess of the fatty acid, its soap or its $C_{1-6}$ ester is present.

After the reaction, unreacted excess alkyl or alkenyl group containing material should remain in the softening material mixture and not be removed by a recrystallization or other purification step as taught in the prior art. The advantages of using an excess alkyl or alkenyl group containing material and not using a recrystallization step in the process include a higher yield of the softening quaternary material, a reduction of the pour point of the softening material, (therefore reducing ester hydrolysis during processing, reducing energy costs and shortening processing time) and providing a safer less expensive preparation means.

The softening material resulting from the method of the invention may comprise a mixture of monoesters, diesters, triesters etc. depending on the base material. According to the method of the present invention the weight ratio of diester to monoester in the softening material is greater than 3:1 since the diester materials provide a greater fabric softening effect than the equivalent monoester. Preferably the weight ratio of diester to monoester is greater than 4:1, more preferably greater than 25:1.

The product obtained after reacting the base material with the ester-forming alkyl or alkenyl group containing materials, optionally followed by one or more further reaction steps, which do not substantially change the ratio of ester linked material to excess material, such as for example neutralization or quaternization, is a homogeneous mixture of the desired ester-linked softener material and the excess of alkyl or alkenyl groups containing materials. This mixture has a lower pour point than the corresponding mixture in the absence of the excess material. Furthermore the in-situ preparation of the homogeneous mixture according to the invention is clearly preferred over the separate preparation of a mixture of ester-linked materials and excess material, because the latter process requires an additional processing step and often does not give the desired homogeneity of the mixture.

Preferably the pour point of the softening material obtained by a method according to the invention is less than 75° C., more preferred less than 65° C., especially preferred less than 60° C.

Preferably a solvent is also present in the softening material to further reduce the pour point of the material. The use of high a concentration of solvent is precluded by the potential hazards posed by storage and processing of compositions containing such high concentrations of flammable or explosive volatiles. Thus, the solvent is preferably present in an amount of up to about 20%, most preferably up to about 10% and the solvent is preferably a $C_{1-3}$ chain alcohol, such as isopropanol, ethanol, glycerol and mixtures thereof.

Softening materials obtained by a method according to the invention may be used for the preparation of fabric conditioning compositions, for example for the preparation of liquid rinse conditioning products comprising an aqueous base wherein the softening materials are dispersed. Also substrates impregnated with the softening materials may advantageously be used for laundry drier purposes.

A preferred method of processing the composition of the invention is to react di-methyl-amino-propane 1,2-diol with varying amounts of tallow fatty acids by mixing the ingredients and heating the mixture for 7 hours at 120° C. followed by heating for 15 hours under vacuum at 185° C. Resulting esterified products may be further processed by suspending the composition in acetone and treating with methyl chloride in a stirred autoclave maintained at 45° C. and 3 atmospheres gauge pressure. Such a reaction should continue until the esterified product is converted into a quaternary ammonium salt. The quaternary salt may be preferably mixed with a solvent to provide a composition having up to about 20% solvent and 80% solids.

The invention will be illustrated by means of the following examples:

EXAMPLE 1

The effect of mole % excess fatty acid on the pour point values of mixtures of fatty acid and the softening diester material of the invention was observed by preparing sixteen (16) mixtures of 1,2-ditallow oxy-3-trimethyl ammonium propane chloride and varying amounts of excess mole % hardened tallow fatty acid. Each sample was heated to form a homogeneous mixture. Eight (8) of the resulting mixtures were mixed with solvent to give compositions containing 80% solids and 20% isopropanol and glycerol.

The pour point value of each of the sixteen samples was determined after the quaternized mixtures were heated for a second time using a Perkin Elmer Series 7 DSC. The results are presented in Table I below:

TABLE 1

| Example | Wt. % HTFA | Mole % Excess HTFA | Molar Ratio HFTA: Softening Material | Pour Point − solvent °C. | Pour Point + solvent °C. |
| --- | --- | --- | --- | --- | --- |
| Control[1] | (low) | <3.0 | 2:1 | 110 | 76.9 |
| 1 | 2.76 | 3.5 | 2.07:1 | 119.4 | 92.9 |
| 2 | 7.5 | 10 | 2.2:1 | 98.3 | 78.0 |
| 3 | 9.54 | 13 | 2.26:1 | 98.3 | 69.4 |
| 4 | 13.35 | 19 | 2.38:1 | 95.9 | 72.1 |
| 5 | 15.4 | 22.5 | 2.45:1 | 93.1 | 71.9 |
| 6 | 27.8 | 47.5 | 2.95:1 | 84.2 | 69.5 |
| 7 | 55.05 | 151 | 5:02:1 | 53.9 | 45.2 |
| 8 | 63.4 | 213.5 | 6.27:1 | 54.1 | 37.7 |

[1]The control sample was prepared as described above except after the quaternary ammonium salt was precipitated it was recrystallized in acetone to remove the excess fatty acid given the final quaternary product as described in Example I of U.S. Pat. No. 4,137,180. This recrystallization step was not carried out in the remaining examples.

As seen above the samples (2–8) having more than 10 mole % excess fatty acid had significantly reduced pour point values compared to the pour point value of the control sample. The control sample was processed with a costly recrystallization step to remove excess fatty acid. Reduction of the control sample pour point was accomplished with solvent alone in the presence of excess fatty acid according to the invention.

*The control sample was prepared as described above except after the quaternary ammonium salt was precipitated it was recrystallized in acetone to remove the excess fatty acid given the final quaternary product as described in Example I of U.S. Pat. No. 4,137,180. This recrystallization step was not carried out in the remaining examples.

Sample 1 having only 3.5 mole % excess fatty acid (2:1 softening material to fatty acid) actually increased the pour point of the prepared sample.

It was further observed when the results were graphed as shown in FIG. 1 that a point of infexion occurred at around 10 mole % fatty acid excess, both when solvent was present and absent.

It is noted that the presence of solvent further reduces the pour point values of the samples, as would be expected from the processing of conventional quaternary compounds such as DHTDMAC.

EXAMPLE 2

It was observed that the pour point values of mixtures of a conventional quaternary compound A (di-hardened tallow dimethyl ammonium chloride) and various amounts of tallow fatty acids actually increased compared to the pour point values of the individual components.

Compound A supplied as Adogen 442-100P and hardened tallow fatty acid supplied as Pristerine 4916 were mixed together as described in Example 1. The pour points of the mixtures were determined using a Perkin Elmer Series 7 DSC, as described above, and the results are presented in Table 2 below:

TABLE 2

| Example | Molar ratio fatty acid:compound A | Mole % Excess HFTA* | Pour point °C. |
| --- | --- | --- | --- |
| Control | — | 100% | 61.05 |
| Control | — | 0% | 68.02 |
| 1 | 2.2:1 | 10% | 92.2 |
| 2 | 2.4:1 | 20% | 90.7 |
| 3 | 1.4:1 | 35% | 91.3 |
| 4 | 1:1 | 50% | 88.7 |

*If the sites of Compound A are considered equivalent to a diester.

It was thus observed that the pour point values of samples having an excess mole % of fatty acid were more than 20° C. higher than the pour point values of Compound A alone or the fatty acid alone.

Based on the foregoing it was observed that the prior art actually teaches away from the use of an excess mole % of an alkyl or alkenyl group containing material to lower the pour point of a mixture of such material with a quaternary ammonium compound. It is especially useful that a mixture of excess material with the softening material of the invention lowers the pour point of the mixture as the pour point of the softening compound is very high, namely, about 110° C.

I claim:

1. A method of preparing a softening material including a quaternary ammonium group comprising:
    (a) selecting a base material comprising a tertiary amine having two $R_1$ groups, each $R_1$ group independently selected from $C_{1-4}$ alkyl, alkenyl or hydroxy alkenyl groups and one 1,2 diol group connected to the nitrogen atom via a $(CH_2)_n$ group wherein n is 0–5;
    (b) selecting an alkyl or alkenyl group containing material in a quantity of more than 10 mole percentage excess of the base material, the material selected from the group consisting of $C_8$–$C_{28}$ monobasic fatty acids;
    (c) esterifying the base material with the alkyl or alkenyl group-containing material; and
    (d) quaternizing the product of step (c) to form a softening material with a pour point of less than 98.3° C., without the presence of solvent, and having a formula

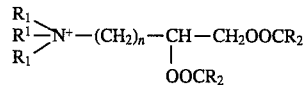

wherein each $R_1$ group is independently selected from $C_{1-4}$ alkyl, alkenyl or hydroxyalkyl groups; and each $R_2$ group is independently selected from $C_{8-28}$ alkyl or alkenyl groups; and n is an integer from 0 to 5, and a weight ratio of diester material to monoester material greater than 3:1, with the provision that the softening material is not recrystallized.

2. A method according to claim 1 wherein the step of selecting the alkyl or alkenyl group containing material comprises selecting more than a 20 mole % excess of the alkyl or alkenyl group containing material.

3. A method according to claim 1 wherein the weight ratio of diester material to monoester material is greater than 4:1.

4. A method according to claim 1 wherein the step of selecting the alkyl or alkenyl group containing material further comprises selecting up to 20 wt. % of a solvent.

5. The method according to claim 4 wherein the solvent is a $C_{1-3}$ alcohol.

6. The method according to claim 1 wherein the softening material has a pour point of less than 75° C.

* * * * *